United States Patent [19]

Cote et al.

[11] Patent Number: 4,613,576

[45] Date of Patent: Sep. 23, 1986

[54] HUMAN MONOCLONAL ANTIBODIES TO CANCER CELLS

[75] Inventors: Richard J. Cote; Donna M. Morrissey; Alan N. Houghton; Edward J. Beattie, Jr., all of New York, N.Y.; Herbert F. Oettgen, New Canaan, Conn.; Lloyd J. Old, New York, N.Y.

[73] Assignee: Sloan-Kettering Institute for Cancer Research, New York, N.Y.

[21] Appl. No.: 473,830

[22] Filed: Mar. 9, 1983

[51] Int. Cl.[4] .............. C12N 15/00; C12N 5/00; G01N 33/53; C12P 21/00
[52] U.S. Cl. .............................. 436/548; 435/7; 435/68; 435/172.2; 435/240; 435/241; 935/93; 935/95; 935/96; 935/99; 935/100; 935/106; 935/108; 935/110
[58] Field of Search ............. 435/172.2, 948, 68, 435/7, 240, 241; 935/93, 95, 96, 99, 100, 106, 108, 110; 436/548

[56] References Cited

U.S. PATENT DOCUMENTS

4,434,230  2/1984  Ritts, Jr. .............................. 435/240

FOREIGN PATENT DOCUMENTS

0073953  3/1980  European Pat. Off. ............ 435/172
0044722  1/1982  European Pat. Off. ............ 435/108
WO82/01461  5/1982  PCT Int'l Appl. .................. 435/240

OTHER PUBLICATIONS

Glassy, M. C. et al., Proc. Natl. Acad. Sci., U.S.A., 80 6327-6331 (1983).

Ueda, R. et al., Proc. Natl. Acad. Sci., U.S.A., 78, 5122-5126 (1981).

Steinitz, et al., EB Virus–Induced B Lymphocyte Cell Lines Producing Specific Antibody, Nature 269, (Sep. 29, 1977) pp. 420–423.

Koskimies, Human Lymphoblastoid Cell Line Producing Specific Antibody Against Rh-Antigen D, Scand. J. Immunol., 11, 73–77 (1980).

Olsson, et al., Human-Human Hybridomas Producing Monoclonal Antibodies of Predefined Antigenic Specificity, Proc. Natl. Acad. Sci., U.S.A., 77, No. 9 (Sep. 1980), pp. 5429–5431.

Croce, et al., Production of Human Hybridomas Secreting Antibodies to Measles Virus, Nature, vol. 288, (Dec. 4, 1980), pp. 488–489.

Nowinski, et al., Human Monoclonal Antibody Against Forssman Antigen, Science, vol. 210, (Oct. 31, 1980), pp. 537–539.

Schlom, et al., Generation of Human Monoclonal Antibodies Reactive with Human Mammary Carcinoma Cells, Proc. Natl. Acad. Sci., U.S.A., 77, No. 11, (Nov. 1980), pp. 6841–6845.

Edwards, et al., A Human-Human Hybridoma System Based on a Fast-Growing Mutant of the ARH-77 Plasma Cell Leukemia-Derived Line, Eur. J. Immunol., 12, pp. 641–648 (1982).

Primary Examiner—Robert J. Warden
Assistant Examiner—L. Krawczewicz
Attorney, Agent, or Firm—Felfe & Lynch

[57] ABSTRACT

Hybridomas which produce human monoclonal antibodies are disclosed. The hybridomas are formed by fusing lymphocytes from individuals with various cancers to an immortal cell line, such as a myeloma, from, e.g., a human cell line, or a mouse cell line.

11 Claims, 1 Drawing Figure

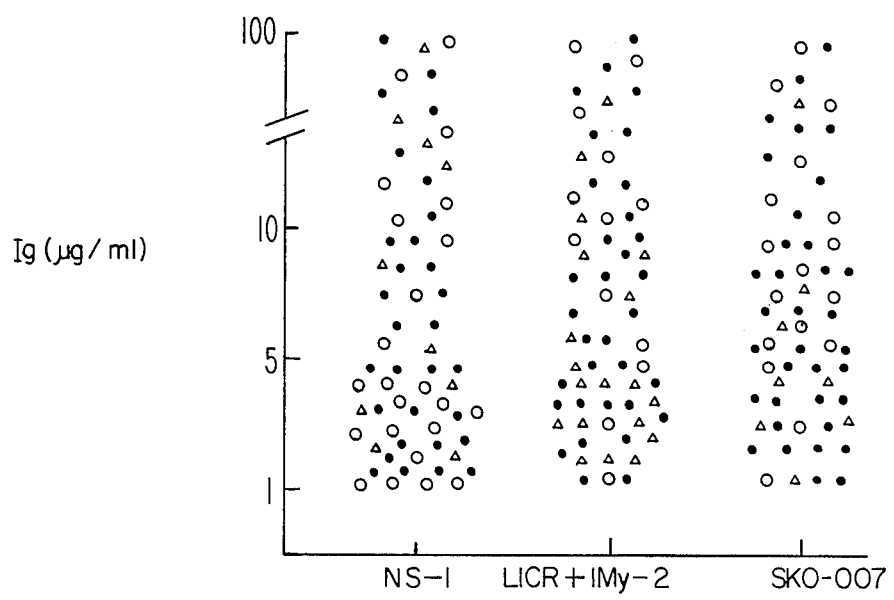

HUMAN MONOCLONAL ANTIBODIES TO CANCER CELLS

This present invention was wholly or partially made with funds provided by the Department of Human Health and Services under Grant No. CA-19765 and CA-08748. Accordingly, the United States Government has certain rights in this invention.

This invention concerns hybridomas which produce human monoclonal antibodies (HmAbs). The hybridomas are formed by fusing an immortal cultured cell line with lymphocytes from individuals having various cancers. The human monoclonal antibodies produced by these hybridomas recognize certain cell surface and intracellular antigens on normal and malignant cells. The use of these human monoclonal antibodies in diagnosis of cancer is disclosed.

BACKGROUND

The serological analysis of human cancer has been revolutionized by the introduction of the hybridoma technology (Köhler, G. & Milstein, C. (1975) Nature 256:495–497. Knowledge about the surface antigenic structure of several types of human cancers has advanced rapidly with mouse monoclonal antibodies as serological probes, and application of these reagents to cancer diagnosis and therapy is underway. Production of human monoclonal antibodies, however, has proved more difficult to achieve. Despite much effort by many laboratories around the world, there are relatively few reports of success in the literature. The two approaches that have been explored most vigorously are transformation of B cells by Epstein-Barr virus (EBV) (Steinitz, M., Klein, G., Koskimies, S. & Makel, O. (1977) Nature 269:420–422, Koskimies, S. (1980) Scand. J. Immunol. 11:73–77. and hybridization of B cells with drug-marked mouse or human myeloma or lymphoblastoid cells lines (Olsson, L. & Kaplan, H. S. (1980) Proc. Nat'l. Acad. Sci., U.S.A. 77:5429–5431, Croce, C. M., Lennenbach, A., Hall, W., Steplewski, Z. & Koprowski, H. (1980) Nature 288488–489, Nowinski, R., Berglund, C., Lane, J., Lostrom, M., Bernstein, I., Young, W., Hakomori, S., Hill, L. & Cooney, M. (1980) Science 210:537–539, Schlom, J., Wunderlick, D. & Teramoto, Y. A. (1980) Proc. Nat'l. Acad. Sci., U.S.A. 77:6841–6845, Lane, H. C., Shelhamer, J. H. Mostowski, H. S. & Fauci, A. S. (1982) J. Exp. Med. 155:333–338). Difficulties in establishing stable antibody-secreting clones has been a major problem with EBV transformation, and a low frequency of hybrid clones resulting from fusion of human lymphocytes with human B cell lines has limited progress with this approach to producing human monoclonal antibodies. Although fusion of human lymphocytes with mouse myeloma results in substantial numbers of hybrids secreting human immunoglobulin (Ig) (Nowinski, R., Berglund, C., Lane, J., Lostrom, M., Bernstein, I., Young, W., Hakomori, S., Hill, L. & Cooney, M. (1980) Science 210:537–539. and Schlom, J., Wunderlich, D. & Teramoto, Y. A. (1980) Proc. Nat'l. Acad.. Sci., U.S.A. 77:6841–6845), there is a general feeling that these interspecies hybrids are rather unstable. Nevertheless, several mouse/human hybrids that continued to secrete Ig for extended periods have been isolated (Nowinski, R., Berglund, C., Lane, J., Lostrom, M., Bernstein, I., Young, W., Hakomori, S., Hill, L. & Cooney, M. (1980) Science 210:537–539. and Lane, H. C., Shelhamer, J. H. Mostowski, H. S. & Fauci, A. S. (1982) J. Exp. Med. 155:333–338).

Edwards et al. (Edwards, P. A. W., Smith, C. M., Neville, A. M. & O'Hare, M. J. (1982) Eur. J. Immunol. 12:641–648) have recently described a hyposanthine guanine phosphoribosyl transferase (HGPRT)-deficient human lymphoblastoid line, LICR-LON-HMy2 (LICR-2), that grows vigorously, has been shown to fuse with human lymphocytes and produces hybrids that secrete human Ig distinguishable from the Ig of the parental line (Edwards, P. A. W., Smith, C. M., Neville, A. M. & O'Hare, M. J. (1982) Eur. J. Immunol. 12:641–648, Sikora, K., Alderson, T. Phillips, J. & Watson, J. V. (1982) Lancet 2:11–14). Efforts have been exerted to use this cell line, and two other cell lines, the SKO-007 line of Olsson and Kaplan (Olsson, L. & Kaplan, H. S. (1980) Proc. Nat'l. Acad. Sci., U.S.A. 77:5429–5431. and the mouse myeloma, NS-1 (Köhler, G. & Milstein, C. (1976) Eur. J. Immunol. 6:511–519) to make hybridomas that produce human Ig antibodies.

SUMMARY

Human monoclonal antibody-producing hybridoma cell lines of the present invention have been formed by fusing immortal cells from human or mouse sources with lymphocytes from individuals having renal cancer, lung cancer, breast cancer or lymphoproliferative disease. The HmAb produced by these hybridomas recognize cell surface and cytoplasmic components of human normal and malignant cells. Normal and cancerous human cells may be detected by immunoassay with these HmAb.

DESCRIPTION

Abbreviations: LICR-2, LICR-LON-HMy2; Ig, immunoglobulin; PHA, phytohemagglutinin; FCS, fetal calf serum; PA, protein A; IA, immune adherence; anti-Ig, rabbit antihuman Ig; EBV, Epstein-Barr virus; PBS, phosphate buffered saline; HmAb(s), human monoclonal antibody(ies).

The following description is intended to illustrate this invention without limiting same in any manner especially with respect to substantially functional equivalents of cell lines described and claimed herein which equivalents can be produced in accordance with the invention following the procedures outlined in the specification of this application.

Availability of Hybridoma Cell Lines

The cell lines disclosed in the present invention are deposited at the American Type Culture Collection, Bethesda, Md. and bear the following deposit numbers:

| Sloan-Kettering # | ATCC # |
| --- | --- |
| Ri 37 | HB 8223 |
| Sm 21 | HB 8237 |
| Po 71 | HB 8238 |
| De 8 | HB 8239 |

Deposit is for the purpose of enabling disclosure only and is not intended to limit the concept of the present invention to the particular materials deposited.

Cell Lines. The ARH-77 derived LICR-2 human lymphoblastoid line was kindly provided by Drs. M. O'Hare, P. Edwards and A. M. Neville, the London Branch of the Ludwig Institute for Cancer Research.

The U266-derived SKO-007 human myeloma line was obtained from Becton-Dickinson (Palo Alto, CA), and was rendered mycoplasmafree by Dr. J. Fogh, Sloan-Kettering Institute for Cancer Research. The mouse myeloma line, NS-1, was obtained in 1979 from Dr. U. Hammerling, Sloan-Kettering Institute for Cancer Research. Characteristics of these cell lines are:

| CELL LINE | HEAVY CHAIN | LIGHT CHAIN | DOUBLING TIME | KARYOTYPE |
|---|---|---|---|---|
| LICR-2 | γ | κ | 24 hr | human |
| SKO-007 | ε | λ | 35 hr | human |
| NS-1 | — | κ | 24 hr | mouse |

The cells were cultured in RPMI 1640 supplemented with 7.5% fetal calf serum, 1% nonessential amino acids (GIBCO, Grand Island, NY), 100 U/ml penicillin, 100 g/ml streptomycin and 20 g/ml 8-azaguanine. No growth occurred in medium containing $4 \times 10^{-7}$M aminopterin.

Source of Lymphocytes. Sterile specimens were obtained from the Pathology Department of Mermorial Hospital through the Tumor Procurement Service. Lymphocytes were derived from (a) regional lymph nodes (12 patients with breast cancer, two patients with lung cancer and one patient with renal cancer); (b) peripheral blood (six patients with renal cancer and three normal individuals); (c) spleen (four patients with lymphoproliferative disease and one patient with renal cancer); and (d) tumor specimens (four lung cancers, four breast cancers and one malignant plural effusion from breast cancer).

Preparation of Lymphocytes. Tumor, lymph nodes and spleen were freed of surrounding normal tissue under steril conditions, and the specimens were minced and passed through 500 m cell sieves. The resultant suspension was pelleted, resuspended in RPMI 1640, layered on Ficoll-Hypaque (Pharmacia, Piscataway, NJ), and centrifuged at 400 g for 20 min. The interface cell population was washed and used as a source of lymphocytes for fusion. Peripheral blood lymphocytes were similarly separated on Ficoll-Hypaque gradients. Lymphocytes ($1-2 \times 10^6$ cells/ml) were incubated in RPMI 1640 medium with 7.5% FCS at 37° C. for 24–48 hrs prior to fusion.

Cell Fusion. Lymphocytes and the myeloma/lymphoblastoid cells were combined at a 1:1 or 2:1 ratio and washed three times in RPMI 1640. After the Final Wash, the supernatant was decanted and 0.2 ml 42% (w/v) polyethylene glycol (m.w. 4000) [in phosphate-buffered saline (PBS) containing 15% (v/v) DMSO] was added slowly to the cell pellet with gentle mixing for 3 min at 37° C. Ten ml RPMI 1640 with 7.5% FCS was then added drop by drop over a 5 minute period, after which the cell suspension was washed and resuspended in port-fusion medium, 15% FCS, penicillin/streptomycin, nonessential amino acids, $2 \times 10^{-5}$M 2-mercaptoethanol, $1 \times 10^{-4}$ hypoxanthine and $1.6 \times 10^{-5}$M thymidine). The cells were incubated overnight at 37° C., pelleted, resuspended in post-fusion medium containing $4 \times 10^{-7}$M aminopterin and plated in 96 well tissue culture plates (Costar 3596) at a density of $1-2 \times 10^5$ lymphocytes/well on feeder layers of BALB/c or C57BL/6 peritoneal cells ($1 \times 10^5$ cells/well, plated 24–48 hrs previously). The medium was changed once a week, and the cells maintained in the presence of $4 \times 10^{-7}$M aminopterin for 4–6 weeks.

Fusion Conditions: General Comments. A number of factors in the fusion procedure were analyzed. Because of variability from fusion to fusion, firm conclusions regarding optimal conditions are difficult to reach. However, several factors were found to influence results in a generally consistent fashion. These included: (1) Condition of myeloma/lymphoblastoid lines. The lines were maintained in log phase growth at 85% cell viability; fusions with overgrown cultures resulted in a low frequency of clonal outgrowth. (2) Fusion ratios. Lymphocyte: myeloma/lymphoblastoid cell ratios of 1:1 or 2:1 resulted in 2–8 times greater clonal outgrowth than fusions at 5:1 or 10:1. (3) Time of aminopterin addition. A delay in the addition of aminopterin to the fused cells for 24 hrs resulted in more vigorous growth of clones. (4) Fetal calf serum (FCS). Significant differences in the frequency of clonal outgrowth were found with different lots of FCS. As initially observed by Edwards et al. (Edwards, P. A. W., Smith, C. M., Neville, A. M. & O'Hare, M. J. (1982) Eur. J. Immunol. 12:641–648), some lots of FCS inhibited the growth and clonability of the myeloma/lymphoblastoid cell lines and the growth of Ig-secreting clones derived from fusions. Lots of FCS were therefore prescreened for optimal growth-promoting properties using these cell types. Optimum fusion success rate was obtained with FCS concentrations of about 10% to 15%. (5) Other media supplements. Medium conditioned by several different cell types did not improve the frequency of clonal outgrowth. Supernatant from cultures of peripheral blood mononuclear cells stimulated 4–6 days with PHA and added to the post-fusion medium resulted in a marked reduction in resulting clones.

Results of Fusions with NS-1, LICR-2 and SKO-007. Clones derived from NS-1 generally appeared between 2–4 wks after fusion, while clones derived from LICR-2 and SKO-007 appeared between 4–7 wks after fusion. All but one fusion between human lymphocytes and NS-1 resulted in growth (95%), while 79% of fusions with LICR-2 and 55% of fusions with SKO-007 resulted in growth (Table I). Fusions of LICR-2 and SKO-007 with peripheral blood lymphocytes gave the poorest results, with only 60% and 40% of fusions resulting in growth, respectively. For a given number of lymphocytes, fusions with NS-1 resulted in an average of eight times more clones than fusions with LICR-2 and 20 times more clones than fusions with SKO-007 (Table I).

| | CELL LINES AND DIFFERENT SOURCES OF HUMAN LYMPHOCYTES | | | | |
|---|---|---|---|---|---|
| | No. Fusions with Growth | No. of Clones per $10^7$ Lymphocytes Fused | | | No. Wells |
| Fusions with | No. Fusions Done | Median | (Range) | % Ig+ Wells* | Screened |
| CELL FUSIONS | | | | | |
| NS-1 | 20/21 | 60.0 | (0–250) | 51% | 867 |
| LICR-2 | 27/34 | 6.9 | (0–74) | 65% | 375 |
| SKO-007 | 12/22 | 1.5 | (0–26) | 47% | 104 |
| LYMPH NODE LYMPHOCYTES | | | | | |

-continued
CELL LINES AND DIFFERENT SOURCES OF HUMAN LYMPHOCYTES

| Fusions with | No. Fusions with Growth / No. Fusions Done | No. of Clones per $10^7$ Lymphocytes Fused Median | (Range) | % Ig+ Wells* | No. Wells Screened |
|---|---|---|---|---|---|
| NS-1 | 7/7 | 49.4 | (6.6–155) | 52% | 431 |
| LICR-2 | 13/15 | 10.6 | (2.5–74) | 61% | 207 |
| SKO-007 | 4/8 | 2.4 | (0–26) | 66% | 38 |
| PERIPHERAL BLOOD LYMPHOCYTES | | | | | |
| NS-1 | 8/8 | 61.3 | (1.5–240) | 42% | 322 |
| LICR-2 | 8/13 | 3.2 | (0–29) | 74% | 57 |
| SKO-007 | 4/10 | 0.75 | (0–17) | 64% | 25 |
| SPLENOCYTES | | | | | |
| NS-1 | 1/1 | 60.0 | | 80% | 60 |
| LICR-2 | 4/4 | 4.0 | (1.4–33) | 70% | 107 |
| SKO-007 | 4/4 | 1.6 | (.67–5.8) | 20% | 41 |
| TUMOR-ASSOCIATED LYMPHOCYTES | | | | | |
| NS-1 | 4/5 | 46.7 | 0–250) | 60% | 54 |
| LICR-2 | 2/2 | 11.6 | (10.6–12.4) | 25% | 4 |

*% wells with growing clones having detectable levels of Ig in the supernatant (500 ng/ml).

There was a statistically significant difference (Student test) in the frequency of outgrowth between clones derived from NS-1 and LICR-2 (p 0.0005), NS-1 and SKO-007 (p. 0.0005) and LICR-2 and SKO-007 (p 0.001). This relationship was consistent and independent of the source of lymphocytes.

Immunoglobulin Detection and Quantitation. Supernatants were screened for the production of human Ig by an enzyme-linked immunoassay. Falcon 3034 plates were precoated with 10 μl of supernatant from wells containing growing clones and incubated overnight at 4° C. The plates were washed with PBS and 10 μl of alkaline phosphatase conjugated goat antihuman γ, μ or α heavy chain-specific antibody (Sigma Chemical Co., St. Louis, MO) was added to each well (1/100 dilution). For determination of total Ig, the class-specific reagents were combined (final dilution of each reagent 1/100). After a 30 min. incubation at 37° C., the plates were washed, and 10 μl of p-nitrophenyl disodium phosphate (1 mg/ml) in 10% diethanolamine buffer (pH 9.6) was added to each well and incubated for 30 min. at 37° C. Color changes were measured by an Artek Model 210 Reader. The test was specific for each Ig class over a range of 500 ng/ml to 50 g/ml. For detection of intracellular-λ or κ light chains by indirect immunofluorescence (see below), goat antihuman λ or κ light chain antibodies conjugated to FITC (Cappel Laboratories, Cochranville, PA) was used (1/40 dilution).

Serological Assays for Cell Surface and Intracellular Antigens. The protein A (PA), immune adherence (IA) and rabbit antihuman Ig (anti-Ig) red cell rosetting assay and absorption tests for the detection of cell surface antigens have been described previously (Shiku, H., Takahashi, T., Oettgen, H. F. & Old, L. J. (1976) J. Exp. Med. 144:873–881, Pfreundschuh, M. G., Ueda, R., Rauterberg, E. W., Dorken, B. H. & Shiku, H. (1980) J. Immunol. Metho. 37:71–81., Albino, A. P., Lloyd, K. O., Houghton, A. N., Oettgen, H. F. & Old, L. J. (1981) J. Exp. Med. 154:1764–1778. Intracellular antigens were detected by indirect immunofluorescene tests with target cells grown to confluency in Falcon 3034 plates. The plates were washed and the cells fixed with a 1:1 methanol:acetone (v/v) solution for 5 min. at room temperature. 10 μl of the supernatant to be tested was plated into each well and incubated for 1 hr. at room temperature. The cells were washed and 10 μl of a goat antihuman Ig conjugated to FITC (DAKO, Copenhagen) was added to each well (1/40 dilution) and incubated for 1 hr. at room temperature. After washing, fluorescence was evaluated with a Leitz Dialux 20 fluorescent microscope. The human cell lines used in the serological assays have been described previously (Shiku, H., Takahashi, T., Oettgen, H. F. & Old, L. J. (1976) J. Exp. Med. 144:873–881, Albino, A. P., Lloyd, K. O., Houghton, A. N., Oettgen, H. F. & Old, L. J. (1981) J. Exp. Med. 154:1764–1778, Ueda, R., Ogata, S. I., Morrissey, D. M., Finstad, C. L., Szkudlarek, J., Whitmore, W. F., Jr., Oettgen, H. F., Lloyd, K. O. & Old, L. J. (1981) Proc. Nat'l. Acad. Sci., U.S.A. 78:5122–5126).

Immunoglobulin Secretion: Range and Stability. Wells with growing clones were screened for Ig secretion; 20–80% contained 500 ng Ig/ml supernatant. [The level of chain secreted by the LICR-2 line (100 ng/ml) was generally below the sensitivity of our Ig assay. However, the possibility that the production of LICR-2-derived chain may be increased following fusion cannot be excluded. Human and mouse light chains and ε heavy chains were not detected in these assays.] The levels of Ig produced by the clones were similar regardless of the myeloma/lymphoblastoid cell line or the source of lymphocytes (FIG. 1). Seventy to 75% of Ig-secreting clones produced between 1–10 μg Ig/ml and 25–30% produced between 11–100 g/ml. In 80–90% of wells, only one class of Ig could be detected. The relative proportion of clones secreting each of the major Ig classes (IgM, IgG, IgA) was independent of the myeloma/lymphoblastoid fusion partner, but appeared to be influenced by the source of lymphocytes. The results of 21 individual fusions are shown in Table II. A difference was found between clones derived from peripheral blood lymphocytes and those derived from axillary lymph nodes of patietns with breast cancer. A higher proportion of IgA-secreting clones resulted from fusions with axillary lymph nodes, while the proportion of IgM-secreting clones was generally higher in fusions with peripheral blood lymphocytes.

TABLE II

IMMUNOGLOBULIN SECRETION OF CLONES DERIVED FROM FUSIONS AND SKO-007: RELATION TO SOURCE OF LYMPHOCYTES

| Lymphocyte Source Client Diag. | Patient Number | Myeloma Lymphoblast- oid Line | No. Lympho- cytes Fused | No. Wells With Growth | % Ig+ Wells* | % Ig+ Wells $\mu$ | $\gamma$ | Producing $\alpha$ |
|---|---|---|---|---|---|---|---|---|
| LYMPH NODE: | | | | | | | | |
| Breast Ca | 1 | NS-1 | $1.0 \times 10^6$ | 55 | 85% | 10% | 50% | 40% |
| Breast Ca | 2 | NS-1 | $1.0 \times 10^7$ | 12 | 67% | 20% | 10% | 70% |
| Breast Ca | 3 | NS-1 | $1.0 \times 10^7$ | 76 | 66% | 21% | 31% | 48% |
| Breast Ca | 4 | LICR-2 | $1.7 \times 10^6$ | 24 | 80% | 18% | 45% | 36% |
| Breast Ca | 5 | LICR-2 | $2.5 \times 10^6$ | 9 | 77% | 30% | 38% | 32% |
| Breast Ca | 6 | LICR-2 | $4.6 \times 10^7$ | 24 | 71% | 19% | 31% | 50% |
| Lung Ca | 7 | NS-1 | $7.5 \times 10^7$ | 50 | 46% | 37% | 22% | 41% |
| Lung Ca | 7 | LICR-2 | $7.5 \times 10^7$ | 53 | 59% | 14% | 61% | 25% |
| Renal Ca | 8 | NS-1 | $3.1 \times 10^6$ | 48 | 40% | 59% | 14% | 27% |
| Renal Ca | 8 | LICR-2 | $4.6 \times 10^6$ | 34 | 47% | 50% | 31% | 19% |
| PERIPHERAL BLOOD: | | | | | | | | |
| Renal Ca | 9 | NS-1 | $2.0 \times 10^6$ | 48 | 90% | 8% | 77% | 15% |
| Renal Ca | 10 | NS-1 | $1.0 \times 10^7$ | 65 | 48% | 35% | 45% | 20% |
| Renal Ca | 11 | NS-1 | $3.7 \times 10^6$ | 35 | 49% | 50% | 50% | 0 |
| Renal Ca | 12 | NS-1 | $1.9 \times 10^7$ | 68 | 29% | 54% | 32% | 14% |
| Renal Ca | 13 | LICR-2 | $2.8 \times 10^7$ | 13 | 31% | 50% | 50% | 0 |
| Renal Ca | 14 | LICR-2 | $1.0 \times 10^7$ | 29 | 83% | 42% | 35% | 23% |
| Renal Ca | 14 | SKO-007 | $1.0 \times 10^7$ | 17 | 70% | 33% | 50% | 17% |
| Renal Ca | 11 | SKO-007 | $3.7 \times 10^6$ | 5 | 80% | 35% | 65% | 0 |
| Normal | 15 | LICR-2 | $1.0 \times 10^7$ | 9 | 89% | 25% | 50% | 25% |
| MALIGNANT PLEURAL | | | | | | | | |
| Breast Ca | 16 | SKO-007 | $1.0 \times 10^7$ | 26 | 73% | 29% | 57% | 14% |
| SPLEEN | | | | | | | | |
| Hodgkin's Disease | 17 | NS-1 | $1.0 \times 10^7$ | 60 | 80% | 50% | 25% | 25% |
| | 18 | LICR-2 | $3.0 \times 10^7$ | 50 | 88% | 37% | 57% | 6% |
| | 19 | SKO-007 | $5.0 \times 10^7$ | 29 | 17% | 0 | 0 | 100% |

Footnote to Table II
*% wells with growing clones having detectable levels of Ig in the supernatant (>500 ng/ml)

The stability of Ig secretion by cells derived from fusions with NS-1, LICR-2 and SKO-007 was compared over a 2-3 month period of subculturing, the percentage of cultures continuing to secrete Ig was comparable (62-70%) in the case of the three fusion partners (Table III). At four and seven months post-fusion, approximately 50% of cultures from NS-1 and LICR-2 fusions continued to produce Ig. Thirty-two NS-1 and 19 LICR-2-derived cultures secreting Ig at two months were cloned (one cell/well) once or twice and stable Ig-secreting clones could be selected in 70-80% of cases (observation period >5 months). In our experience, the loss of LICR-2-derived Ig-secreting clones was due to cell loss rather than instability of Ig production, because cultures derived from LICR-2 fusions were found to clone more poorly than those from NS-1 fusions.

Antibody Reactivity. 422 Ig-secreting cultures were tested for the production of antibody reactive against cell surface or intracellular antigens using tissue culture lines as target cells (Table IV). Less than 1% of the cultures showed detectable antibody to cell surface antigens, while 9% produced antibody to intracellular antigens.

Specificity of a Human Monoclonal IgG Reactive with a Cell Surface Antigen

A clone derived from a fusion of NS-1 and lymphocytes from an axillary lymph node of a patient with breast cancer (Ri37) was found to produce an IgG antibody that identifies a cell surface antigen detected on certain cancer cell lines and on mononuclear cells from peripheral blood.

TABLE III

STABILITY OF IMMUNOGLOBULIN SECRETION BY CLONES RESULTING FROM FUSIONS WITH NS-1, LICR-2 AND SKO-007*

| Ioma/Lympho- stoid Lines | No. Fusions Studied | Cultures Ig+ 2-3 Months Post-Fusion | Cultures Ig+ 4 Months Post-Fusion | Cultures Ig+ 6-7 Months Post-Fusion |
|---|---|---|---|---|
| NS-1 | 5 | 39/63 (62%) | 30/52 (58%) | 15/28 (53%) |
| LICR-2 | 7 | 36/51 | 14/27 (52%) | 14/27 (52%) |
| SKO-007 | 4 | 24/34 (70%) | — | |

Immunoglobulin detectable in culture supernatant at levels >500 ng/ml.
Ocnominator indicates number of Ig+ cultures detected at 1-2 months post-fusion and selected for further study. For results of cloning, see text.
Three Ig+ cultures from fusions with SKO-007 were subcloned. They remained stable for Ig production over a 5-month period.

REACTIVITY OF IMMUNOGLOBULINS PRODUCED BY CULTURES DERIVED FROM FUSIONS OF HUMAN (LYMPHOCYTES WITH NS-1, LICR-2) SKO-007*

| Lymphocyte Source: | Antigen Site | FUSION PARTNER | | |
|---|---|---|---|---|
| | | NS-1 | LICR-2 | SKO-007 |
| LYMPH NODE | Cell Surface | 1/141 | 0/65 | 0/29 |
| | Intracellular | 8/141 | 2/65 | 1/29 |
| PERIPHERAL BLOOD | Cell Surface | 1/77 | 1/26 | 0/9 |
| | Intracellular | 6/77 | 2/26 | 0/9 |
| SPLEEN | Cell Surface | 0/30 | 0/41 | 0/4 |

-continued

REACTIVITY OF IMMUNOGLOBULINS PRODUCED BY
CULTURES DERIVED FROM FUSIONS
OF HUMAN (LYMPHOCYTES WITH NS-1, LICR-2)
SKO-007*

| Lymphocyte Source: | Antigen Site | FUSION PARTNER | | |
|---|---|---|---|---|
| | | NS-1 | LICR-2 | SKO-007 |
| | Intracellular | 13/30 | 5/41 | 1 |

Reactivity to cell surface antigens tested by the PA, IA and antihuman Ig assays. Reactivity to intracellular antigens tested by indirect immunofluorescence.(see Materials & Methods).Panel human cell lines: Breast Ca: MCF-7, CAMA, BT-20; Lung Ca: SK-LC-2, SK-LC-5, SK-LC-6, aw; Melanoma: SK-MEL-41, SK-MEL-131; Astrocytoma: U251 MG; Colon Ca: SW-12222; ladder Ca: 253J, ICC-SUP, Scab; Renal Ca: SK-RC-7, KyRc; Normal Kidney, Ky, Nem.
Number of cultures with antibody reactivity/number of Ig+ cultures tested.

The culture producing this antibody has been subcloned five times (one cell/well) and contains both human and mouse chromosomes. It has been stable for antibody production over a 12-month period and secretes 2–5 g IgG/ml of culture supernatant. The antibody is detected by both PA and anti-Ig assays, but not by IA assays. Absorption tests show that the antigen is expressed by 11 of the 87 different cell types tested (Table V).

Reactivity with Intracellular Antigens

Thirty-eight cultures from fusions with NS-1, LICR-2 and SKO-007 have been identified that secrete antibody reactive with cytoplasmic, cytoskeletal, perinuclear or nuclear structures. Fusion of peripheral blood lymphocytes from normal individuals as well as from tumor-bearing patients has resulted in cultures reacting with intracellular antigens. Nine of the 38 cultures have been subcloned two or more times, and have remained stable for antibody production; six clones were derived from fusions with NS-1, two from LICR-2 and one from SKO-007.

Intracellular antigens of cultured human tumor cells were detected by hybrids derived from fusions of human lymphocytes with NS-1 (A) Sm21: IgM. Lymphocyte source: lymph node, breast cancer (cytoplasmic); (B) Po71: IgM. Lymphocyte source: spleen, Hodgkin's Disease (perinuclear structure); (C) De8: Igm. Lymphocyte source: peripheral blood, renal cancer (cytoskeletal, nucleolar).

Characterization of Clones. Karyotypic analysis of six clones derived from NS-1 fusions with human lymphocytes and secreting human Ig showed both mouse and human chromosomes. The hybrid nature of selected LICR-2 and SK0-007 derived clones has been demonstrated by the presence of new species of light and/or heavy chains in the clonal population.

TABLE V

ABSORPTION ANALYSIS OF AN IgG HUMAN MONOCLONAL ANTIBODY (RI37) PRODUCED BY A NS-1
DERIVED HYBRID AND REACTIVE WITH A CELL
SURFACE ANTIGEN OF NORMAL AND MALIGNANT CELLS

| Ri37 REACTIVE CELLS | | Ri37 NONREACTIVE CELLS | |
|---|---|---|---|
| | Titer Direct Anti-Ig Assay | | |
| LUNG CANCER | | LUNG CANCER | COLON CANCER |
| SK-LC-6 | 1:50,000 | SK-LC-5,7,12,13,16 | SW-1083,1116,1222,HT-29 |
| SK-LC-8 | no titer | MELANOMA | BLADDER CANCER |
| SK-LC-LL | no titer | SK-MEL-13,19,23,28, 33,37,93-II, MeWo | J253, 639-V, Scaber |
| MELANOMA | | | T CELL LEUKEMIAS AND |
| SK-MEL-41 | 1:100,000 | OVARIAN CANCER | LYMPHOMAS |
| SK-MEL-151 | 1:1000 | SK-OV-3 | P-12, CCRF-CEM, MOLT-4 HPB-ALL, C-45 |
| | | CERVICAL CANCER | |
| BLADDER CANCER | | ME-180, CAPAN-2 | B CELL LYMPHOMAS |
| TCC-SUP | 1:2000 | | SK-DHL-2, SU-DHL-10, |
| | | ASTROCYTOMA | Raji (Burkitt's lymphoma |
| PERIPHERAL BLOOD MONONUCLEAR CELLS 5 individuals tested. | Tested by absorption only. | U251 MG, AE, AJ, AS, BD, BO, CE | BALL-1 (B cell leukemia) |
| | | | IBV-TRANSFORMED B CELL |
| | | BREAST CANCER | BD, FG, DX, AZ, AV |
| | | BT-20, AlAb, CAMA, SK-BR-5, MDA-MB-157, | RED BLOOD CELLS |
| | | MDA-MB-231, MDA-MB-361, ZR-75-1 | Fetal, Newborn, I+, A,B,O, Rh+, Rh−, Sheep RBC |
| | | RENAL CANCER | |
| | | SK-RC-1,2,4,6,7,9,28, | NORMAL KIDNEY |
| | | Caki-1 | KM, DZ, FO, ES, KN |

Equal volumes of packed cells and Ri37 supernatant diluted 1:1000 to 1:2000 were mixed and incubated for 1 hr at room temperature. After removal of absorbing cells by centrifugation, residual reactivity was tested on SK-MEL-41 target cells by the anti-Ig assay.

Nine Ig secreting LICR-2-derived clones were examined for intracytoplasmic light chain production by immunofluorescence. Three of nine clones were producing a new λ light chain in addition to the κ light chain of the LICR-2; five produced only κ light chain and one produced only λ light chain. Three Ig-secreting SKO-007 derived clones were similarly studied. Two were producing a new κ light chain in addition to the λ light chain of the SKO-007 line; one produced only the λ light chain. Analysis by SDS-PAGE has shown γ and κ chains in SKO-007 derived clones and μ and λ light chains in LICR-2-derived clones.

Human lymphocytes from lymph node, peripheral blood, spleen and tumor specimens have been fused with the immortal cell lines LICR-LON-HMy2 (abbreviated LICR-2) or SKO-007 human cell lines, or the NS-1 mouse myeloma line. Over 80 fusions using the three myeloma/lymphoblastoid lines have been performed. Several factors appeared to improve the fusion outcome, including maintenance of the myeloma/lymphoblastoid lines in log phase growth at 95% viability, a delay of 24 hrs in the introduction of aminopterin to the fused cells, and preselection of the fetal calf serum used in the medium. For a given number of lymphocytes, fusions with NS-1 produced 5–20 times more clones than fusions with LICR-2 or SKO-007, and LICR-2 produced four times as many clones as SKO-007. The percentage of clones secreting human immunoglobulin, the range of immunoglobulin production, and the proportion of IgM, IgA and IgG secretors were comparable for clones derived from the three myeloma/lymphoblastoid lines. In addition, the stability of human immunoglobulin production was similar for the LICR-2 and NS-1-derived clones over extended periods, and is comparable to the stability achieved with mouse/mouse hybridomas. A number of stable clones producing human monoclonal antibodies reacting with cell surface, cytoplasmic or nuclear antigens have been isolated from tumor-bearing patients and normal individuals. A new surface antigenic system present on normal and malignant cells has been defined with a human monoclonal antibody derived from a patient with breast cancer. Techniques for producing human monoclonal antibody now appear to be sufficiently advanced to initiate a serological dissection of the humoral immune response to human cancer.

What is claimed:

1. Human monoclonal antibody producing hybridoma cell line where the product of said cell line specifically binds to cell surface antigen system HB 8223.

2. Human monoclonal antibody producing hybridoma cell lines where the product of said cell lines specifically bind to intracellular antigens HB 8237, HB 8238 or HB 8239.

3. Human monoclonal antibodies which specifically bind to cell surface antigen HB 8223 or intracellular antigens HB 8237, HB 8238, or HB 8239.

4. An immunoassay for human cells comprising contracting said cells with at least one monoclonal antibody selected from the group consisting of HB 8223, HB 8237, HB 8238, HB 8239 under conditions favoring formation of an antigen:antibody complex between said antibody and an antigen or antigens to which said antibodies specifically bind, and observing the formation of said complex or the absence of said formation.

5. Immunoassay of claim 4 with human monoclonal antibody HB 8223.

6. Immunoassay of claim 4 with human monoclonal antibody HB 8237.

7. Immunoassay of claim 4 with human monoclonal antibody HB 8238.

8. Immunoassay of claim 4 with human monoclonal antibody HB 8239.

9. Method of diagnosis of tumors comprising immunoassay of claim 4 of an excised human specimen.

10. Method of detecting cytoplasmic cytoskeletal perinuclear and nuclear components of human cells comprising immunoasay of claim 4 of said cells with human monoclonal antibody HB 8237, HB 8238, or HB 8239.

11. Panel of phenotyping human monoclonal antibodies comprising HB 8223, HB 8237, HB 8238, and HB 8239.

* * * * *